(12) United States Patent
Kirsch et al.

(10) Patent No.: US 7,376,256 B2
(45) Date of Patent: May 20, 2008

(54) METHOD FOR ANALYZING CHEMICAL AND OR BIOLOGICAL SAMPLES BY MEANS OF PARTICLE IMAGES

(75) Inventors: Achim Kirsch, Hamburg (DE); Olavi Ollikainen, Tallinn (EE)

(73) Assignee: Evotec Oai AG, Hamburg (DE)

( * ) Notice: Subject to any disclaimer, the term of this patent is extended or adjusted under 35 U.S.C. 154(b) by 0 days.

(21) Appl. No.: 10/471,043

(22) PCT Filed: Apr. 16, 2003

(86) PCT No.: PCT/EP03/03960

§ 371 (c)(1),
(2), (4) Date: Jul. 27, 2004

(87) PCT Pub. No.: WO03/088123

PCT Pub. Date: Oct. 23, 2003

(65) Prior Publication Data

US 2004/0248191 A1 Dec. 9, 2004

(30) Foreign Application Priority Data

Apr. 16, 2002 (DE) ................................ 102 16 683

(51) Int. Cl.
*G06K 9/50* (2006.01)
(52) U.S. Cl. ................ 382/133; 436/546; 436/172
(58) Field of Classification Search ................ 436/172, 436/546; 382/133, 134
See application file for complete search history.

(56) References Cited

U.S. PATENT DOCUMENTS 3,879,706 A * 4/1975 Favier et al. ................ 382/134
5,003,616 A * 3/1991 Orita et al. .................. 382/282
5,989,835 A 11/1999 Dunlay et al.
6,137,899 A * 10/2000 Lee et al. .................... 382/133
6,631,331 B1 * 10/2003 Sabry et al. .................. 702/19
6,944,338 B2 * 9/2005 Lock et al. .................. 382/168

FOREIGN PATENT DOCUMENTS

| EP | 0 902 394 A1 | 3/1999 |
| WO | WO 99/39184 | 8/1999 |
| WO | WO 99/45366 | 9/1999 |
| WO | WO 01/84106 A2 | 11/2001 |

OTHER PUBLICATIONS

Messina, Joseph P. et al, "2.5D morphogenesis: Modeling landuse and landcover dynamics in the Ecuadorian Amazon", Plant Ecology, vol. 156, No. 1, Sep. 2001, pp. 75-88, Philadelphia, PA, USA.
International Search Report, completed Jul. 29, 2003.

* cited by examiner

*Primary Examiner*—Jill Warden
*Assistant Examiner*—Natalia Levkovich
(74) *Attorney, Agent, or Firm*—Griffin & Szipl, P.C.

(57) ABSTRACT

A method for analyzing chemical and/or biological samples comprises the production of a particle image (42) of at least one particle included in the sample. Subsequently, a particle surface (10) of the at least one particle included in the particle image (42) is divided into particle zones (14,18). According to the invention, zone-dependent particle data are subsequently acquired in different states (z1, z2, z3), which then can be evaluated.

25 Claims, 4 Drawing Sheets

State Z1    State Z2    State Z3

METHOD FOR ANALYZING CHEMICAL AND OR BIOLOGICAL SAMPLES BY MEANS OF PARTICLE IMAGES

This is a National Phase Application in the United States of International Patent Application No. PCT/EP03/03960 filed Apr. 16, 2003, which claims priority on German Patent Application No. DE 102 16 683.8, filed Apr. 16, 2002.

The invention relates to a method for analyzing chemical and/or biological samples by means of particle images, which is adapted to be performed particularly in high- or medium-throughput screening installations.

BACKGROUND OF THE INVENTION

For analyzing biological and/or chemical activities of substances or particles and/or molecules present in the substances, data of the samples to be analyzed are acquired. For acquiring data, microscopes, particularly confocal microscopes, are used. In doing so, certain components of a sample are marked with fluorescent markers, where it is possible to draw conclusions with respect to reactions within the sample on the basis of the emission of fluorescence of these markers.

The reaction of a cell to a particular substance can be detected, for example, by the migration of a molecule marked with a fluorescent marker, for example, into the nucleus. An analyzing method suitable therefor is described in U.S. Pat. No. 5,989,835. In this method, the nucleus of a cell is marked or colored in a first step. The coloring is performed with a fluorescent marker that may be stimulated by a UV laser. Further, a transcription factor in the cytoplasm surrounding the nucleus is marked with another fluorescent marker. By stimulating the nucleus with a UV laser and a threshold value method, a mask separating the nucleus from the cytoplasm is prepared. Subsequently, the mask is reduced in size so that it is guaranteed that a substantially circular first portion is exclusively arranged within the nucleus. In the next step, the mask border is enlarged so that a ring is created which exclusively lies in the cytoplasm. By comparing the two cell portions, for example, it can be detected that an active substance marked with a color marker has migrated into the nucleus, since the luminosity of the two portions changes in this case.

First, this method described in U.S. Pat. No. 5,989,835 has the disadvantage that the nucleus has to be located. This is only possible by using special colors or special color markers since it has to be ensured that they react with the nucleus to be able to detect the position of the nucleus. The color markers used in this case, Hoechst 33342 and 33258, for example, can only be stimulated by a UV laser. The acquisition of UV lasers, however, is expensive, and they have high operational costs due to their high cooling water consumption. Another disadvantage of the afore-described method consists in that meaningful results can only be achieved if the ring is arranged completely within the cytoplasm. This is not the case, for example, when the nucleus is arranged in the border portion of the cytoplasm. Another disadvantage of the afore-described method consists in that always a definitely defined surface in the form of the nucleus is defined and detected. Thus, the method is expensive and inflexible.

It is the object of the invention to provide an analyzing method for chemical and/or biological samples where the trouble with detecting changes of the sample is reduced.

This object is solved, according to the invention, by the method for analyzing chemical and/or biological samples, particularly with high-throughput or medium-throughput screening installations, with the steps of: respectively producing at least one particle image (42) of at least one sample with at least one particle being included in the sample, respectively; (b) defining several particle zones (14,18; 22,24; 32,34,36) independent of subparticular compartments; (c) acquiring particle data of the sample independently of the zone; and (d) evaluating the acquired particle data.

SUMMARY OF THE INVENTION

According to the method according to the invention, which is particularly suitable for high- and medium-throughput screening installations, particle images of at least one sample are produced in a first step. These images include at least one particle, e.g., a cell, included in the sample. Typically, each image includes more than 10, particularly more than 50 particles, particularly cells. Producing the particle image is effected, for example, by means of a microscope and/or an image acquisition means such as a CCD camera that may be connected with a suitable image evaluating means.

According to the invention, particle zones are defined which are independent of subparticular compartments. In this connection, the zones are preferably arranged or defined within a particle image.

Preferably, a particle surface, i.e., the surface occupied by a particle included in the produced image, is divided into several particle zones. In this case, the particle surface is defined by the fact that the foreground differs from the background in the particle image. To this end, a threshold value can be preset which defines the boundary between background and foreground. In dependence on the selected threshold value, the particle surface defined in the particle image comprises the actually present surface of the particle or possibly a surface slightly smaller or larger. Preferably, the particle surface is plane. In this case, it is advantageous to use confocal microscopes since definite planes within the sample can be defined by confocal microscopes so that a definite particle surface can be defined in the particle image.

Each particle surface of the particle images which are preferably produced independently of each other of at least one sample are divided into particle zones according to the invention. The division of the particle zones is effected independently of subparticular compartments. If the particles are cells, for example, the division of the particle surface into particle zones is effected independently of subcellular compartments such as, for example, nuclei, mitochondria, lysosomes etc. Preferably, the particle surface is divided into at least five, particularly preferably into at least ten particle zones.

According to the invention, for example, several zone images of a single sample can be produced at different points of time. Then, these zone images can be, for example, compared with each other for evaluation. It is as well possible to produce particle images of several samples at the same points of time and to compare them with each other. In this case, for example, one sample may serve as reference sample to which no reagent has been added. A combination of these two procedures is also possible.

It is also possible that several particle images are acquired and at least one particle zone is defined that extends over several particle images. This is a particle zone that is not arranged within a preferably plane particle surface but in space. Such a particle zone may have a plane or spatial configuration. In case of a spatial configuration, defined geometric shapes such as cuboids, cubes or the like are preferred.

In the next step, particle data of the sample or possibly of different samples and the particle images, respectively, are acquired in dependence on the zones. Thus, for example, an acquisition of the medium luminosity of individual zones with different samples is effected. The individually produced particle images of several samples show the particles in different states since, for example, different reagents added to the samples cause different reactions in the samples. In one sample, for example, a reagent marked with a marker will penetrate into the cell and in another sample, it will stay outside the cell plasm. In this case, the acquired luminosities of the individual zones of the different particle images are different, for example, whereas the acquired luminosities of the individual zones were substantially identical for all samples before the addition of the different reagents. The particle data acquired in this connection are then evaluated in the next step. Because of a luminosity shift within the particle zones, for example, conclusions can be drawn with respect to the movement of active substances marked with a color marker or the like. Instead of using color markers, the characteristic radiation of suitable particles can be detected as well. Here, the fluorescence of color markers as well as the characteristic radiation may be in the visible as well as in the invisible range.

According to the method according to the invention, it is thus not required to add a special color for marking the nucleus or the like to the sample since the position of the nucleus, for example, does not have to be known for carrying out the method according to the invention. Other subparticular compartments do not have to be determined in detail either for carrying out the method according to the invention. The particle surface is rather divided into particle zones independent of subparticular compartments. Thus, it is not required to use corresponding colors that can only be stimulated by a UV laser expensive in acquisition and operation. Thus, the costs of the analyzing method can be considerably reduced. Since, for example, the definition of the individual particle and cell zones, respectively, is independent of the position of the nucleus in the analysis of cells, the described problems occurring with the position of the nucleus at the border of the cytoplasm in the method described in U.S. Pat. No. 5,989,835 cannot occur with the method according to the invention. Thus, the method according to the invention is considerably more flexible.

Preferably, a definition of the particle zones is respectively effected before the acquisition and subsequent evaluation of the particle data.

Preferably, several samples including a plurality of particles each are analyzed simultaneously in the method according to the invention. In doing so, the produced particle images of the samples are compared. At the same point of time, the individual samples are in respectively different states. By comparing the particle images, i.e., the individual zones of the particle images, a migration of a reagent provided with a color marker, for example, or other changes within the particle can be perceived.

Further, it is possible to define particle zones such that they lie outside the particle. By the same comparisons of the particle zones, movements of color markers outside the particles can be perceived, for example.

Preferably, the sample is colored before the particle image will be produced. By these colorations which can be done with conventional colors such as fluorescent markers, the cells or the liquid surrounding the cells is colored, for example. By this coloration, the boundary of the cells and the particles, respectively, can be detected. It is not required to use special colors for coloring the nuclei. Since the particle boundaries can be detected better by coloring the sample, the particle surface of the individual particles can be determined more easily by an image processing system, confocal microscopes or other confocal optics means being preferably used for determining the particle surfaces to be able to acquire particularly individual particles, particularly cells, existing in a particular plane of the sample. Particularly upon coloring the sample, it is essential that the foreground of the sample can be distinguished from the background of the sample by the image processing system, particularly the confocal microscope. The exact particle boundary does not have to be determined. It is rather sufficient when a particle image can be produced wherein at least a large part of the particle is divided into particle zones.

Preferably, the definition of the particle zones is effected such that the entire particle surface is divided into particle zones. The individual particle zones are thus immediately adjacent to each other without any clearance. This has the advantage that movements of, for example, active substances marked with a color marker can be observed closely. It is thus possible to detect movement directions of individual or several active substances or the like. Further, it is possible to define zones outside the particle surface as well. Thereby, it can be detected by a luminosity comparison, for example, how many of the particles marked with a color marker are respectively located within and without a particle, such as a cell. The border portions of the particle zones may also comprise portions directly next to the particle so that these are mixed zones. According to the invention, however, the particle boundary is preferably determined by coloring the sample, for example, so that either only particle zones are defined or particle zones and outer zones or only outer zones can be defined.

When evaluating the particle data, it is possible, according to the invention, not to acquire the particle data of all zones but to acquire the particle data of selected zones only. It is possible, for example, to observe only a border zone extending along the boundary line of the particle and to evaluate its particle data only. It is also possible to observe only the differences of the luminosities of a single zone per particle image.

Preferably, the definition of the particle zones is effected according to a mathematical model. Preferably, in this connection, mathematical models are used which are suited to the reactions to be expected. The starting point is a particle image, respectively.

Further, upon defining the particle zones, it is possible to define them in such a manner that all zones have the same surface area. This is particularly advantageous upon comparing the medium luminosities of individual zones with each other since the luminosity change cannot be caused or influenced by a dimensional change of the zone.

The method according to the invention is particularly suitable for analyzing samples including cells. Preferably, a particle included in the sample is a cell which may form part of a cell compound. Particularly, the particle exclusively consists of one or more cells. With respect to the preferred analysis of cells, the core of the invention therefore consists in that several cell zones independent of subcellular compartments are preferably defined in a particle surface, i.e., a cell surface.

Preferably, the particle state, particularly the cell state, is analyzed in dependence on substances added to the sample. In this connection, the method according to the invention is particularly well suited to drug screening. Samples of different cell states are analyzed, for example, the cell state particularly comprising apoptosis, necrosis, translocation of cellular components, internalization of membraneous molecules or molecule complexes, cell differentiation, morphological appearance, splitting of subcellular compartments and/or generation of subcellular compartments.

BRIEF DESCRIPTION OF THE DRAWINGS

Hereinafter, the invention will be explained in detail with respect to preferred embodiments with reference to the accompanying drawings. In the Figures.

DETAILED DESCRIPTION OF THE INVENTION

Hereinafter, three different methods according to the invention, for dividing particle surfaces into particle zones, are explained with respect to FIGS. 1-3.

Figure 1:
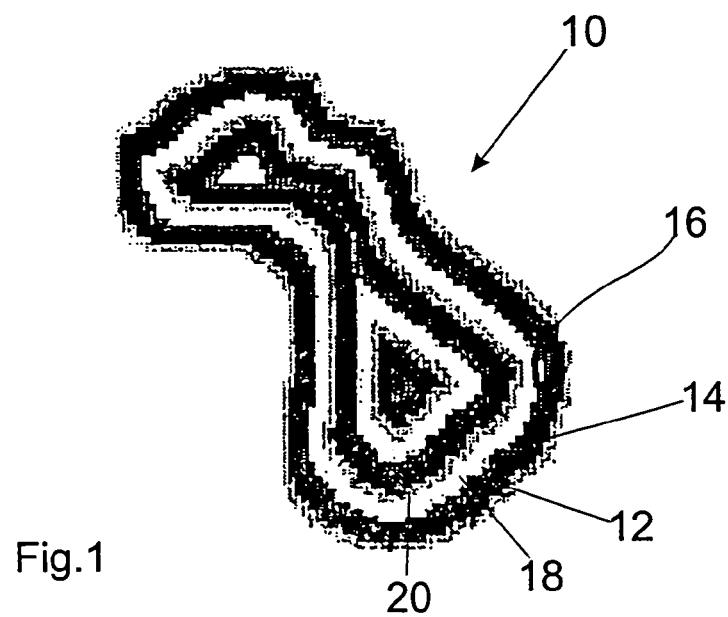
FIGS. 1-3 show sketches of particle zones defined by different methods.

In FIG. 1, a particle surface 10 is illustrated, the outer line 12 representing the boundary line of the particle, such as the cell. The boundary line need not necessarily be the exact boundary of the particle. According to the invention, it is rather sufficient to define a boundary between the background and the foreground preset in dependence on a predetermined threshold value as a boundary line. In this case, the division of the particle surface into particle zones is effected by the fact that each zone has an inner and an outer boundary line. An outer zone 14, for example, has the boundary line 12 as an outer boundary line and the boundary line 16 as an inner boundary line. The next zone 18 farther inward has the boundary line 16 as an outer boundary line and the boundary line 20 as an inner boundary line and so forth. The definition of the boundary lines 16,20 is effected by the fact that each of them has a substantially constant distance to the particle boundary 12.

Thus, the individual zones 14,18 can also be described by the following formula, for example, which defines the interval of the distance to the particle boundary:

$$(N*\Delta d, N*\Delta d + \Delta d)$$

where N=0, 1, . . . and $\Delta d$ is a width of the zone.

By the above formula, the distance of individual strip-shaped zones 14,18 to the particle boundary 12 is thus defined in dependence on $\Delta d$. In this connection, it is decisive that all zones 14,18,20 have the same width.

With this method, it is further possible to also define zones arranged outside the particle surface 10.

Figure 2:
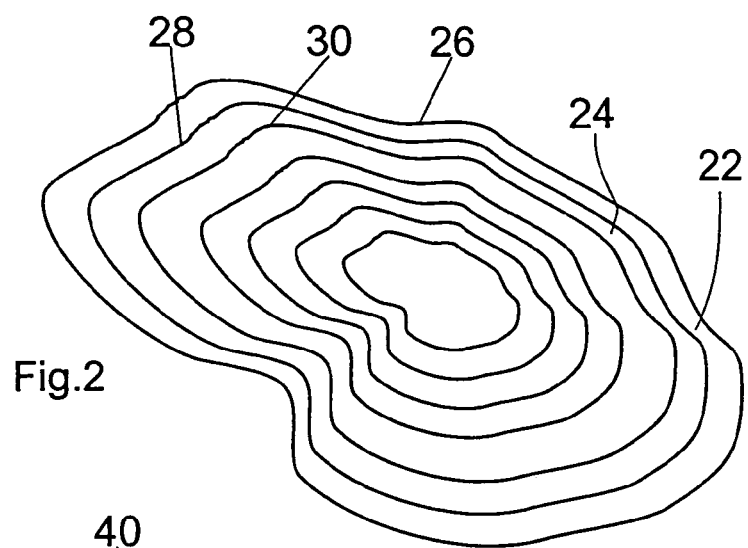

FIG. 2 shows another method for determining particle zones 22,24. The particle zones 22,24 defined here are also divided from each other by boundary lines 26,28,30. The zones 22,24, however, do not have the same width. For determining these zones, concentric boundary lines 26,28,30 are rather used. Thus, the boundary lines 26,28,30 have similar geometric shapes. Stated in simplified terms, the boundary line 28 may be produced by a percental reduction of the size of the boundary line 26.

For defining the zones of one of the two methods apparent in FIGS. 1 and 2, the definition of boundary lines is not absolutely necessary. The method may also be performed by dividing the particle image into individual pixels and defining the affiliation of a pixel to the one or the other zone by mathematical formulas. This results in boundary lines between the adjacent particle zones, of course.

Figure 3:
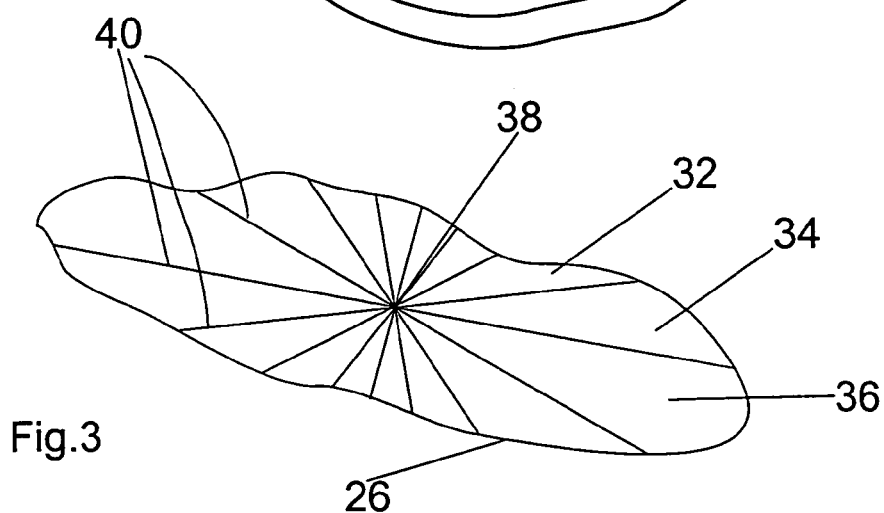

Different particle zones 32,34,36 etc. can also be defined with a method apparent from FIG. 3. Here, a main point 38 is defined, which is, for example, the most luminous point within the particle surface 10, the geometric center or the center of gravity. Starting from this point, preferably radially extending boundary lines 40 serving to delimit the particle zones 32,34,36 etc. are defined. Preferably, the aperture angle of the individual boundary lines 40 is constant. The individual boundary lines may also be arranged such that the surface areas of the zones 32,34,35 are constant.

Figure 4:
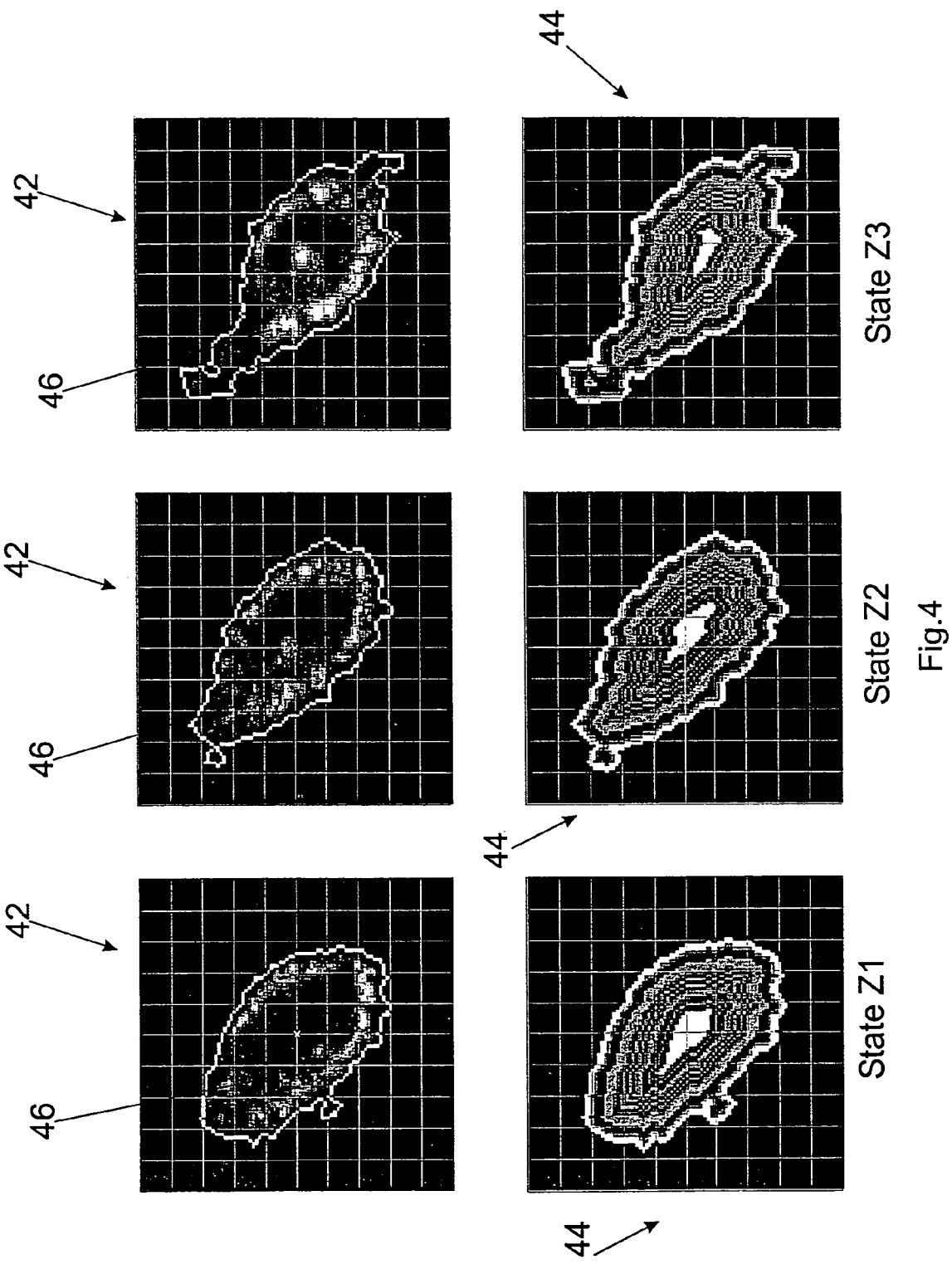
FIG. 4 shows particle images of an analyzed example in different states.
Figure 5:
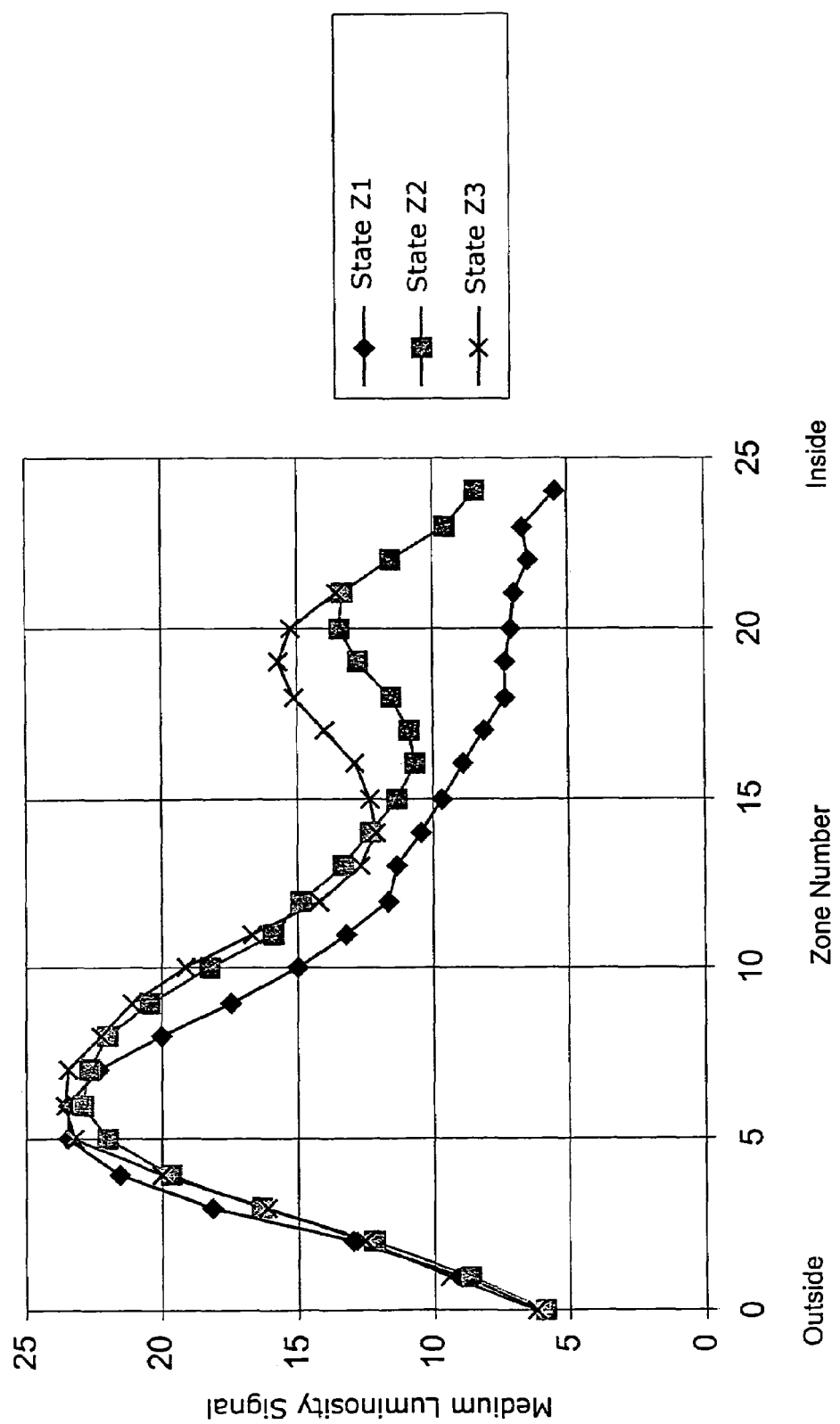
FIG. 5 shows a diagram of the medium luminosity signals with reference to the individual zones of the particle images illustrated in FIG. 4.

In the first example for explaining the method according to the invention represented with respect to FIGS. 4 and 5, three particle images 42 are illustrated in FIG. 4, which show different states z1, z2, and z3 of various particle images 44 from different samples. Further, the zone images 44 to the corresponding states are illustrated, in which zone images the cells 46 have been divided into zones by means of the method described in detail with respect to FIG. 1.

In the illustrated example, different reagents are introduced into several identical samples. After a fixed time interval of possibly several hours, the samples of which there are three in the illustrated example are observed and a particle image 46 as well as a zone image 44 is prepared of each of the three samples. Thus, three different zone images 44 are prepared which represent different states z1, z2, and z3 in the three samples. In the first sample that is on the left in FIG. 4, there was no reaction to the substrate added to the sample. In dependence on the individually defined zones, this results in the course illustrated in FIG. 5 with respect to the state z1. In the second sample illustrated in the middle of FIG. 4, the substrate has caused a reaction. Here, the substrate has migrated into the interior of the cell. It is apparent from the diagram in FIG. 5 that this has resulted in an increase in luminosity in the region of the numerals 20-23 which represent corresponding zones. A corresponding luminosity increase is also apparent in the third sample on the right in FIG. 4. This, in turn, is particularly apparent from the diagram illustrated in FIG. 5 in the region of the numerals 17-20.

Figure 6:
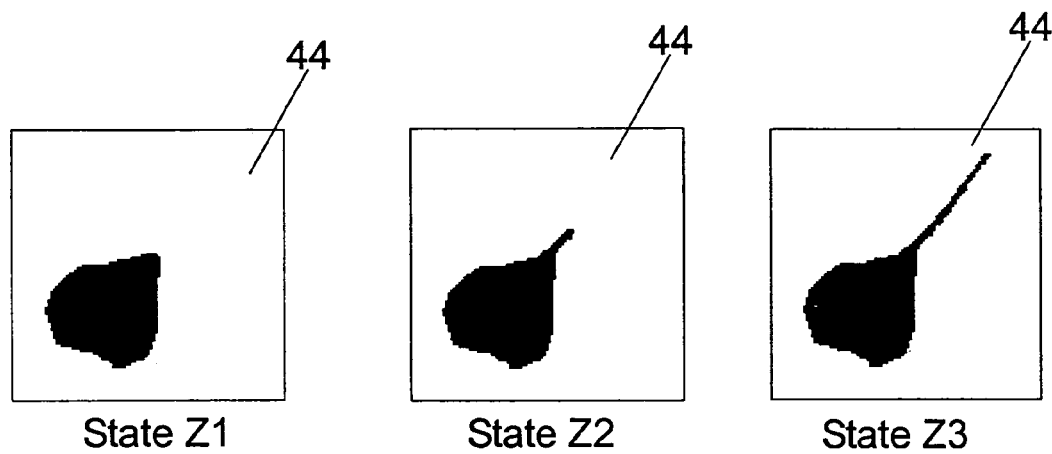
FIG. 6 shows particle images of a further analyzed example in different states.
Figure 7:
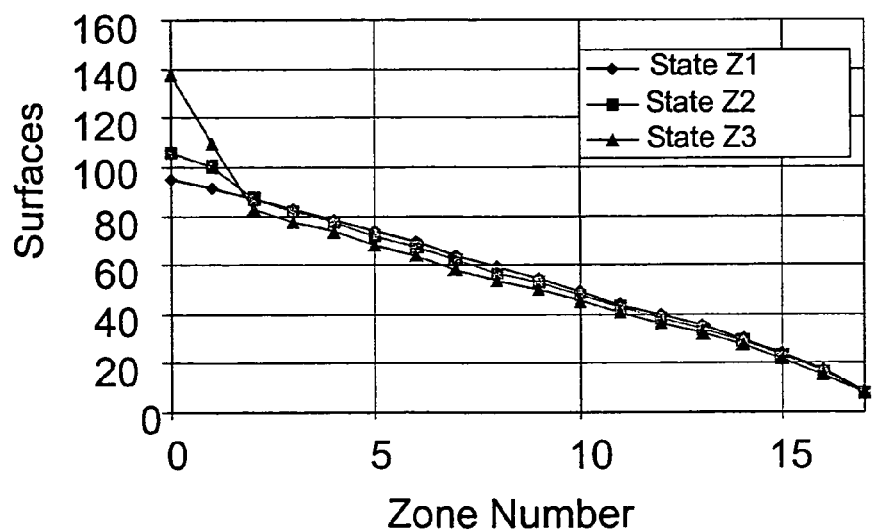
FIG. 7 shows a diagram of the surface over the zones of the particle images illustrated in FIG. 6.

From the example illustrated in FIGS. 6 and 7, it can be seen that the growth of axons in nerve cells can be simply detected by means of the method according to the invention.

In FIG. 6, three particle images 44 are illustrated in different states z1, z2, and z3. The cell, in turn, is divided into individual particle zones by means of the zone definition method described in FIG. 1, said particle zones not being illustrated in detail here. In the illustrated example, in turn, different substrates have been added to three samples. After a preset time interval that may, in turn, possibly last several hours, the three samples are analyzed. A particle image as well as a particle image 44 are produced of each of the samples. Then, the three particle images 44 show different states z1, z2, and z3 of different cells, i.e., states in the individual samples. It is already apparent from the representations in FIG. 6 that particularly the cells in the third sample (right image in FIG. 6) react to the added substrate and form long axons. In the middle sample, an axon was formed as well, although it was not so long. In the left sample, it is apparent that no reaction has occurred. Depending on the length of the formed axon, the size of the surface of the outer zone increases differently in different samples. This is particularly apparent from the diagram illustrated in FIG. 7. The surface of the outer zone illustrated on the left in FIG. 7 is larger in the state z3 than in the state z1. Thus, it is only possible to detect in which cells axons have grown and in which cells they have not grown by comparing the curves illustrated in FIG. 7.

The invention claimed is:

1. Method for analyzing chemical and/or biological samples with high-throughput or medium-throughput screening installations, comprising the steps of:

producing one or more particle images of at least one sample with at least one particle, having a particle surface, being included in the sample;

defining several particle zones of the particle surface by determining a particle boundary before the particle zones are defined and defining a main point within the particle surface and boundary lines extending radially therefrom to the particle boundary, wherein the several particle zones of the particle surface are defined independent of subparticular compartments;

acquiring particle data of the sample in dependence on the particle zones; and evaluating the acquired particle data.

2. Method according to claim 1, wherein a plurality of particle images are produced and at least one particle zone is defined that extends over several particle images of the plurality of particle images.

3. Method according to claim 1, wherein several particle images are produced of several samples.

4. Method according to claim 1, wherein the particle zones are defined within the particle surface of the at least one particle included in the particle image.

5. Method according to claim 1, wherein substantially the entire particle surface is divided into particle zones.

6. Method according to claim 1, wherein the particle zones are defined immediately before the acquisition of the particle data.

7. Method according to claim 1, wherein several particle images are produced of the at least one sample at different points of time.

8. Method according to claim 7, wherein different states of the at least one particle included in the sample are compared with each other when evaluating the acquired particle data.

9. Method according to claim 1, wherein samples of different particle states are analyzed at different times.

10. Method according to claim 1, wherein the sample is colored before the particle image is produced.

11. Method according to claim 1, wherein the boundary lines extending radially from the main point to the particle boundary define first, second and third particle zones.

12. Method according to claim 1, wherein the most luminous point within the particle surface is defined as the main point.

13. Method according to claim 1, wherein the radially extending boundary lines have a substantially identical aperture angle with respect to each other.

14. Method according to claim 1, wherein each individual particle zone of the several particle zones is defined so that each individual particle zone has substantially the same surface area as each of the other individual particle zones.

15. Method according to claim 1, wherein individual particle zones of the several particle zones are selected for analysis in dependence on selection criteria.

16. Method according to claim 8, wherein particle data acquired in dependence on the particle zones includes size of the particle zones in different states of the at least one particle.

17. Method according to claim 8, wherein particle data acquired in dependence on the particle zones includes luminosity of the particle zones in different states of the at least one particle.

18. Method according to claim 1, wherein the at least one particle is a cell and particle zones, independent of subcellular compartments, are defined.

19. Method according to claim 18, wherein the cell forms part of a cell compound comprising one or more cells.

20. Method according to claim 18, wherein samples of different cell states are analyzed and the cell state comprises one or more of components selected from the group consisting of apoptosis, necrosis, translocation of cellular components, internalization of membranous molecules or molecule complexes, cell differentiation, morphological appearance, splitting of subcellular compartments and generation of cellular compartments.

21. Method according to claim 20, wherein the cell state is influenced by adding chemical substances, biological substances, or chemical and biological substances.

22. Method according to claim 21, wherein the cell state is influenced by adding potential pharmacological active substances.

23. Method according to claim 1, wherein the particle surface is divided into at least five particle zones.

24. Method according to claim 23, wherein the particle surface is divided into at least ten particle zones.

25. Method according to claim 1, further comprising the steps of:

presetting a threshold value for defining a boundary between background and foreground in the one or more particle images; and defining the particle surface by a difference between the background and the foreground that exceeds the threshold value.

* * * * *